US010954299B2

(12) United States Patent
Gosset et al.

(10) Patent No.: US 10,954,299 B2
(45) Date of Patent: Mar. 23, 2021

(54) METHODS AND PHARMACEUTICAL COMPOSITIONS FOR THE TREATMENT OF PULMONARY BACTERIAL INFECTIONS

(71) Applicants: INSERM (INSTITUT NATIONAL DE LA SANTÉ ET DE LA RECHERCHE MÉDICALE), Paris (FR); CENTRE NATIONAL DE LA RECHERCHE SCIENTIFIQUE (CNRS), Paris (FR); INSTITUT PASTEUR DE LILLE, Lille (FR); UNIVERSITÉ DE LILLE 1 SCIENCES ET TECHNOLOGIES, Villeneuve d'Ascq (FR); UNIVERSITÉ DE DROIT ET DE LA SANTÉ DE LILLE 2, Lille (FR)

(72) Inventors: Philippe Gosset, Lille (FR); Fahima Madouri, Lille (FR); Muriel Pichavant, Lille (FR)

(73) Assignees: INSERM (Institut National de la Santé et de la Recherche Médicale), Paris (FR); Centre National de la Recherche Scientifique (CNRS), Paris (FR); Institut Paseur de Lille, Lille (FR); Universitéde Lille, Lille (FR)

( * ) Notice: Subject to any disclaimer, the term of this patent is extended or adjusted under 35 U.S.C. 154(b) by 0 days.

(21) Appl. No.: 16/303,391

(22) PCT Filed: May 24, 2017

(86) PCT No.: PCT/EP2017/062346
§ 371 (c)(1),
(2) Date: Nov. 20, 2018

(87) PCT Pub. No.: WO2017/202813
PCT Pub. Date: Nov. 30, 2017

(65) Prior Publication Data
US 2019/0144539 A1    May 16, 2019

(30) Foreign Application Priority Data
May 24, 2016   (EP) .................................... 16305598

(51) Int. Cl.
C07K 16/28   (2006.01)
C07K 16/24   (2006.01)
A61P 31/04   (2006.01)
A61K 45/06   (2006.01)
C12N 15/115  (2010.01)
A61K 39/00   (2006.01)

(52) U.S. Cl.
CPC .............. C07K 16/28 (2013.01); A61K 45/06 (2013.01); A61P 31/04 (2018.01); C07K 16/24 (2013.01); C07K 16/2866 (2013.01); C12N 15/115 (2013.01); A61K 2039/505 (2013.01); C07K 2317/76 (2013.01)

(58) Field of Classification Search
None
See application file for complete search history.

(56) References Cited

U.S. PATENT DOCUMENTS

| 2002/0042366 | A1  | 4/2002  | Thompson et al. | |
|---|---|---|---|---|
| 2005/0170468 | A1* | 8/2005  | Xu | A61P 31/04 |
|              |     |         |    | 435/70.21 |
| 2019/0330330 | A1* | 10/2019 | Gosset | C07K 16/2866 |

FOREIGN PATENT DOCUMENTS

WO    2016/083304 A1    6/2016

OTHER PUBLICATIONS

Broquet A et al: "Interleukin-22 Neutralization Enhanced Mice Susceptibility to Pulmonary Pseudomonas aeruginosa Infection", Abstracts Book, Interscience Conference on Antimicrobial Agents & Chemotherapy (ICAAC), American Society for Microbiology, US, Jan. 1, 2015.
A Broquet et al: "Poster: Interleukin-22 neutralization enhanced mice susceptibility to pulmonary Pseudomonas aeruginosa infection", Sep. 21, 2015.
Yunfeng MA et al: "INterleukin 24 as a novel potential cytokine immunotherapy for the treatment of infection", Microbes and Infection, Elsevier, Paris, FR, vol. 13, No. 12, pp. 1099-1110, Jun. 26, 2011.
Sascha Rutz et al: "The IL-20 subfamily of cytokines—from host defence to tissue homeostasis", The Journal of Immunology, vol. 14, No. 12, pp. 783-795, Nov. 25, 2014.
Ian A Myles et al: "Signaling via the IL-20 receptor inhibits cutaneous production of IL-1[beta] and IL-17A to promote infection with methicilin-resistant *Staphylococcus aureus*", Nature Immunology, vol. 14, No. 8, pp. 804-811, Jun. 23, 2013.
Daniel H Kaplan: "The IL-20 cytokine subfamily: bad guys in host defense?", Nat. Immunol, vol. 9. No. 11, pp. 774-775, Aug. 1, 2013.

* cited by examiner

*Primary Examiner* — Sean McGarry
(74) *Attorney, Agent, or Firm* — W & C IP

(57) ABSTRACT

The present invention relates to methods and pharmaceutical compositions for the treatment of pulmonary bacterial infections. The increasing burden of antimicrobial resistance coupled with the decreasing number of antibiotics in development has urged for strategies to elaborate new therapies. The inventors showed a therapeutic effect of IL-20 receptor 10 antagonists in pulmonary bacterial infection mouse model. Indeed, they demonstrated that treatment with IL-20 receptor antagonists reduces bacterial burden, cellular infiltration and inflammation in bronchoalveolar lavage fluid (BALF) and lung. In particular, the present invention relates to an antagonist of IL-20 cytokines, or/and an antagonist of IL-20RB receptor for use in a method for the treatment of pulmonary bacterial infections in a subject in 15 need thereof.

8 Claims, 5 Drawing Sheets
Specification includes a Sequence Listing.

METHODS AND PHARMACEUTICAL COMPOSITIONS FOR THE TREATMENT OF PULMONARY BACTERIAL INFECTIONS

FIELD OF THE INVENTION

The present invention relates to methods and pharmaceutical compositions for the treatment of pulmonary bacterial infections.

BACKGROUND OF THE INVENTION

Pulmonary bacterial infections are a major health problem and pose a large economic burden on our society. Pulmonary bacterial infections can be caused by a wide range of bacteria, resulting in mild to life-threatening illnesses that require immediate intervention.

For example, *Streptococcus pneumoniae* (pneumococcus) causes respiratory tract infections among infants and the elderly worldwide. Capsular polysaccharide is the main virulence factor, and its composition defines 91 serotypes of pneumococcus. Certain serotypes colonize asymptomatically the human nasopharynx representing a reservoir for inter-individual transmission of the bacteria. In some individuals colonization may progress to pneumococcal pneumonia and invasive disease.

The treatment of pulmonary bacterial infections is most often achieved by using antibiotics which either aim at killing invading bacteria (anti-bacterial mode of action) or inhibiting their growth (bacteriostatic mode of action) without harming the host. Antibiotic effectiveness depends on their mechanism of action, the drug distribution, the site of infection, the immune status of the host, and the presence or not of bacterial resistance factors. Antibiotics work through several mechanisms; some inhibit the formation of bacterial cell walls. Others interrupt bacterial protein synthesis. Yet some others inhibit metabolism or interfere with DNA synthesis and/or cell membrane permeability.

It is however becoming more evident, that antibiotics do not always perform to the extent they should. Some infections cannot be cleared, even if the pathogen is sensitive to the used antibiotic. This inability to completely kill all bacteria poses a severe problem once the antibiotic treatment is stopped, as the infection relapses and the patients fall ill anew. Moreover, the constant antibiotic pressure and the natural competence of some strains results in frequent resistance to antibiotics. The increasing burden of antimicrobial resistance coupled with the decreasing number of antibiotics in development has urged for strategies to maximize the therapeutic index of existing antibiotics. Moreover, immuno-compromised patients are more susceptible to pulmonary infections and the efficiency of antibiotics is lower in these patients.

SUMMARY OF THE INVENTION

The present invention relates to methods and pharmaceutical compositions for the treatment of pulmonary bacterial infections. In particular, the present invention is defined by the claims.

DETAILED DESCRIPTION OF THE INVENTION

The inventors showed a therapeutic effect of IL-20 receptor antagonists in pulmonary bacterial infection model. In particular, they demonstrated that treatment with IL-20 receptor antagonists reduces bacterial burden, cellular infiltration and inflammation in bronchoalveolar lavage fluid (BALF) and lung.

A first aspect of the present invention relates to a method of treating pulmonary bacterial infection in a subject in need thereof comprising administering the subject with a therapeutically effective amount of an antagonist of IL-20 cytokines, or/and an antagonist of IL-20RB receptor.

As used herein, the term "subject" denotes a mammal, such as a rodent, a feline, a canine, and a primate. Preferably, a subject according to the invention is a human.

As used herein, the term "pulmonary bacterial infection" has its general meaning in the art and relates to any infectious disease involving the lungs. Pulmonary bacterial infection can be caused by any bacteria species.

In one embodiment, the bacteria which cause bacterial respiratory tract infections include, but not limited to, the *Aquaspirillum* family, *Azospirillum* family, *Azotobacteraceae* family, *Bacteroidaceae* family, *Bartonella* species, *Bdellovibrio* family, *Campylobacter* species, *Chlamydia* species (e.g., *Chlamydia pneumoniae*), *Clostridium*, *Enterobacteriaceae* family (e.g., *Citrobacter* species, *Edwardsiella*, *Enterobacter aerogenes*, *Erwinia* species, *Escherichia coli*, *Hafnia* species, *Klebsiella* species, *Morganella* species, *Proteus vulgaris*, *Providencia*, *Salmonella* species, *Serratia marcescens*, and *Shigella flexneri*), *Gardinella* family, *Haemophilus influenzae*, *Halobacteriaceae* family, Helicobacter Family, *Legionallaceae* family, *Listeria* species, *Methylococcaceae* family, mycobacteria(e.g., *Mycobacterium tuberculosis*), *Neisseriaceae* family, *Oceanospirillum* family, *Pasteurellaceae* family, *Pneumococcus* species, *Pseudomonas* species, *Rhizobiaceae* family, *Spirillum* Family, *Spirosomaceae*family, *Staphylococcus* (e.g., methicillin resistant *Staphylococcus aureus* and *Staphylococcus pyrogenes*), *Streptococcus*(e.g., *Streptococcus enteritidis*, *Streptococcus Fasciae*, and *Streptococcus pneumoniae*), *Vampirovibr Helicobacter* Family, and *Vampirovibrio* family.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. The term "treatment" encompasses the prophylactic treatment. As used herein, the term "prevent" refers to the reduction in the risk of acquiring or developing a given condition, or the reduction or inhibition of the recurrence or said condition in a subject who is not ill, but who has been or may be near a subject with the disease.

As used herein, the term "IL-20RB" has its general meaning in the art and denotes interleukin-20 receptor subunit beta. Interleukin-20 receptor is a type II cytokine receptor and it is a heterodimer of $\alpha$ and $\beta$ subunits. IL20RB and IL20RA form a heterodimeric receptor for interleukin-20 (Blumberg et al., 2001).

SEQ ID NO: 1: Isoform 1 IL-20 receptor subunit beta
```
          10         20         30         40
  MQTFTMVLEE IWTSLFMWFF YALIPCLLTD EVAILPAPQN 50         60         70         80
  LSVLSTNMKHL LMWSPVIAP GETVYYSVEY QGEYESLYTS 90        100        110        120
  HIWIPSSWCS LTEGPECDVT DDITATVPYN LRVRATLGSQ 130        140        150        160
  TSAWSILKHP FNRHSTILTR PGMEITIDGF HLVIELEDLG 170        180        190        200
  PQFEFLVAYW RREPGAEEHV KMVRSGGIPV HLETMEPGAA 210        220        230        240
  YCVKAQTFVK AIGRYSAFSQ TECVEVQGEA IPLVLALFAF 250        260        270        280
  VGFMLILVVV PLFVWKMGRL LQYSCCPVVV LPDTLKITNS 290        300        310
  PQKLISCRRE EVDACATAVM SPEELLRAWI S
```

SEQ ID NO: 2: Isoform 2 IL-20 receptor subunit beta
```
          10         20         30         40
  MKHLLMWSPV IAPGETVYYS VEYQGEYESL YTSHIWIPSS 50         60         70         80
  WCSLTEGPEC DVTDDITATV PYNLRVRATL GSQTSAWSIL 90        100        110        120
  KHPFNRNSTI LTRPGMEITK DGFHLVIELE DLGPQFEFLV 130        140
  AYWRREPGAE ERPFPWYWPC LPLLASC
```

As used herein, the term "IL-20RB antagonist" has its general meaning in the art and refers to any compound that blocks, suppresses, or reduces (including significantly) the biological activity of inhibits the activity of IL-20RB receptor, or to any compound that inhibit IL-20RB gene expression.

As used herein, the term "IL-20 cytokines" has its general meaning in the art and refers to a subgroup in the IL-10 cytokine family which comprises IL-19 (Exemplary Human NCBI Reference Sequence: NP_715639.1), IL-20 (Exemplary Human NCBI Reference Sequence: NP_061194.2), IL-22, IL-24 (Exemplary Human NCBI Reference Sequence: NP_006841.1) and IL-26. However, among these cytokines, we can distinguish the subgroup of IL-20 cytokines (IL-19, IL-20 and IL-24) which are characterized by their ability to bind receptors including the IL-20RB chain. In contrast, IL-22 and IL-26 acts through their binding to receptors dependent of the IL-10RB chain. IL-19, IL-20 and IL-24 act via a receptor complex that consists of the IL-20R1 and IL-20R2 chains present on epithelial and antigen-presenting cells. IL-20 and IL-24 are additionally able to signal via a second receptor complex (IL-22R1/IL-20R2). Examples of human receptors for IL-20 cytokines include hIL-20R1 (also known as CRF2-8; IL-20RA; IL-20R-alpha) (Exemplary Human NCBI Reference Sequence: NP_055247.3), hIL-20R2 (also known as IL-20RB; IL-20R-beta) (Exemplary Human NCBI Reference Sequence: NP_653318.2) and hIL-22R1 (Exemplary NCBI Reference Sequence: NP_067081.2). More particularly, sequences of human receptors for IL-20 cytokines have been described; for example, in U.S. Pat. Nos. 6,610,286; 7,122,632; 7,393,684; and 7,537,761; and U.S. Pat. App. Pub. Nos. 2006/0263850 A1; 2006/0263851 A1; 2008/0247945 A1, and 2009/0074661 A1. Interestingly, the different reparation and sequences of both IL-20R chains in comparison with those of the IL-22 receptor is essential in order to explain the opposite effect of IL-20 cytokines and Il-22 during bacterial infections.

SEQ ID NO: 3: Isoform 1 Interleukin-20
```
          10         20         30         40         50
  MKASSLAFSL LSAAFYLLWT PSTGLKTLNL GSCVIATNLQ EIRNGFSEIR 60         70         80         90        100
  GSVQAKDGNI DIRILRRTES LQDTKPANRC CLLRHLLRLY LDRVFKNYQT 110        120        130        140        150
  PDHYTLRKIS SLANSFLTIK KDLRLCHAHM TCHCGSEAMK KYSQILSHFE 160        170
  KLEPQAAVVK ALGELDILLQ WMEETE
```

SEQ ID NO: 4: Isoform 2 Interleukin-20
```
          10         20         30         40         50
  MKASSLAFSL LSAAFYLLWT PSTGLKTLNL GSCVIATNLQ EIRNGFSEIR 60         70         80         90        100
  GSVQAKDGNI DIRILRRTES LQDTKPANRC CLLRHLLRLY LDRVFKNYQT 110        120        130        140        150
  PDHYTLRKIS SLANSFLTIK KDLRLCLEPQ AAVVKALGEL DILLQWMEET

E
```

SEQ ID NO: 5: Isoform 1 Interleukin-19
```
          10         20         30         40         50
  MKLQCVSLWL LGTILILCSV DNHGLRRCLI STDMHHIEES FQEIKRAIQA 60         70         80         90        100
  KDTFPNVTIL STLETLQIIK PLDVCCVTKN LLAFYVDRVF KDHQEPNPKI 110        120        130        140        150
  LRKISSIANS FLYMQKTLRQ CQEQRQCHCR QEATNATRVI HDNYDQLEVH 160        170
  AAAIKSLGEL DVFLAWINKN HEVMFSA
```

-continued

SEQ ID NO: 6: Isoform 2 Interleukin-19
```
         10         20         30         40         50
MCTELAFPHR SACSLPLTHV HTHIHVCVPV LWGSVPRGMK LQCVSLWLLG 60         70         80         90        100
TILILCSVDN HGLRRCLIST DMHHIEESFQ EIKRAIQAKD TFPNVTILST 110        120        130        140        150
LETLQIIKPL DVCCVTKNLL AFYVDRVFKD HQEPNPKILR KISSIANSFL 160        170        180        190        200
YMQKTLRQCQ EQRQCHCRQE ATNATRVIHD NYDQLEVHAA AIKSLGELDV

210
FLAWINKNHE VMFSA
```

SEQ ID NO: 7: Isoform 3 Interleukin-19
```
         10         20         30         40         50
MKLQCVSLWL LGTILILCSV DNHGLRRCLI STDMHHIEES FQEIKRAIQA 60         70         80         90        100
KDTFPNVTIL STLETLQIIK PLDVCCVTKN LLAFYVDRVF KDHQEPNPKI 110        120        130        140        150
LRKISSIANS FLYMQKTLRQ CVSHWVRIPA SAPCLPKERP GSAGPHRPPD 160        170        180        190        200
MVLGVKGNSL RTSTGRTVEN LSQWPLLPQG SLPADNSSDG LLLDNPPGVT

NLCQHIP
```

SEQ ID NO: 8: Isoform 1 Interleukin-24
```
         10         20         30         40         50
MNFQQRLQSL WTLARPFCPP LLATASQMQM VVLPCLGFTL LLWSQVSGAQ 60         70         80         90        100
GQEFHFGPCQ VKGVVPQKLW EAFWAVKDTM QAQDNITSAR LLQQEVLQNV 110        120        130        140        150
SDAESCYLVH TLLEFYLKTV FKNYHNRTVE VRTLKSFSTL ANNFVLIVSQ 160        170        180        190        200
LQPSQENEMF SIRDSAHRRF LLFRRAFKQL DVEAALTKAL GEVDILLTWM

QKFYKL
```

SEQ ID NO: 9: Isoform 2 Interleukin-24
```
         10         20         30         40         50
MNFQQRLQSL WTLASRPFCP PLLATASQMQ MVVLPCLGFT LLLWSQVSGA 60         70         80         90        100
QGQEFHFGPC QVKGVVPQKL WEAFWAVKDT MQAQDNITSA RLLQQEVLQN 110        120        130        140        150
VSDAESCYLV HTLLEFYLKT VFKNYHNRTV EVRTIKSFST LANNFVLIVS 160        170        180        190        200
QLQPSQSNEM FSIRDSAHRR FLLFRRAFKQ LDVEAALTKA LGEVDILITW

MQKFYKL
```

SEQ ID NO: 10: Isoform 3 Interleukin-24
```
         10         20         30         40         50
MNFQQRLQSL WTLASRPFCP PLLATASQMQ MVVIPCLGFT LLLWSQVSGA 60         70         80         90        100
QGQEFHFGPC QVKGVVPQKL WEAFWAVKDT MQAQDNITSA RLLQQEVLQN 110        120        130        140        150
VSQENEMFSI RDSAHRRFLL FRRAFKQLDV EAALTKALGE VDILLTWMQK

FYKL
```

SEQ ID NO: 11: Isoform 4 Interleukin-24
```
         10         20         30         40         50
MNFQQRLQSL WTLASKLRIT SRVPGCCSRR FCRTSRKKMR CFPSETVHTG

60
GFCYSGEFESN SWT
```

As used herein, the term "IL-20 cytokines antagonist" has its general meaning in the art and refers to any compound that blocks, suppresses, or reduces (including significantly) the biological activity of IL-20 cytokines or to any compound that inhibit IL-20 cytokines gene expression.

In particular, the anti-IL20 cytokines antagonist is an antagonist of IL-19, IL-20 or/and IL-24.

In some embodiments, the IL-20 cytokines antagonist or/and IL-20RB receptor antagonist is a small organic molecule. The term "small organic molecule" refers to a molecule of a size comparable to those organic molecules generally used in pharmaceuticals. The term excludes biological macromolecules (e. g., proteins, nucleic acids, etc.). Preferred small organic molecules range in size up to about 5000 Da, more in particular up to 2000 Da, and most in particular up to about 1000 Da.

In some embodiments, the IL-20 cytokines antagonist or/and the IL-20RB receptor antagonist is an antibody or a portion thereof. In some embodiments, the IL-20 cytokines antagonist or/and the IL-20RB receptor antagonist is an antibody such as chimeric antibodies, humanized antibodies or full human monoclonal antibodies.

As used herein, "antibody" includes both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or nonhuman antibody. A nonhuman antibody may be humanized by recombinant methods to reduce its immunogenicity in man.

In one embodiment of the antibodies or portions thereof described herein, the antibody is a monoclonal antibody. In one embodiment of the antibodies or portions thereof described herein, the antibody is a full human monoclonal antibody. In one embodiment of the antibodies or portions thereof described herein, the antibody is a polyclonal antibody. In one embodiment of the antibodies or portions thereof described herein, the antibody is a humanized antibody. In one embodiment of the antibodies or portions thereof described herein, the antibody is a chimeric antibody. In one embodiment of the antibodies or portions thereof described herein, the portion of the antibody comprises a light chain of the antibody. In one embodiment of the antibodies or portions thereof described herein, the portion of the antibody comprises a heavy chain of the antibody. In one embodiment of the antibodies or portions thereof described herein, the portion of the antibody comprises a Fab portion of the antibody. In one embodiment of the antibodies or portions thereof described herein, the portion of the antibody comprises a F(ab')2 portion of the antibody. In one embodiment of the antibodies or portions thereof described herein, the portion of the antibody comprises a Fc portion of the antibody. In one embodiment of the antibodies or portions thereof described herein, the portion of the antibody comprises a Fv portion of the antibody. In one embodiment of the antibodies or portions thereof described herein, the portion of the antibody comprises a variable domain of the antibody. In one embodiment of the antibodies or portions thereof described herein, the portion of the antibody comprises one or more CDR domains of the antibody.

Antibodies are prepared according to conventional methodology. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with antigenic forms of IL-20RB or IL-20 cytokines. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes. Briefly, the recombinant IL-20RB or IL-20 cytokines may be provided by expression with recombinant cell lines. In particular, IL-20RB or IL-20 cytokines may be provided in the form of human cells expressing IL-20RB or IL-20 cytokines at their surface. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

Significantly, as is well-known in the art, only a small portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

This invention provides in certain embodiments compositions and methods that include humanized forms of antibodies. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3 A of the CDRs in a three dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

As will be apparent to one of ordinary skill in the art, the present invention also provides for F(ab')2, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4.

In another embodiment, the antibody according to the invention is a single domain antibody. The term "single domain antibody" (sdAb) or "VHH" refers to the single heavy chain variable domain of antibodies of the type that can be found in Camelid mammals which are naturally devoid of light chains. Such VHH are also called "Nanobody®".

Examples of anti-IL-20 antibodies include, but are not limited to, those disclosed in U.S. Pat. Nos. 7,435,800; 7,115,714; 7,119,175; 7,151,166; and 7,393,684; and PCT publications WO 2007/081465; WO 99/27103; WO 2004/085475; and WO 2005052000. In some embodiments, the anti-IL-20 antibody described herein is anti-IL-20 antibody 7E, which refers to monoclonal antibody mAb 7E and its functional variants. MAb 7E is produced by the hybridoma cell line deposited at the American Type Culture Collection, 10801 University Boulevard, Manassas, Va. 20110-2209, U.S.A. and assigned a deposit number PTA-8687. This hybridoma cell line will be released to the public irrevocably and without restriction/condition upon granting a US patent on this application, and will be maintained in the ATCC for a period of at least 30 years from the date of the deposit for the enforceable life of the patent or for a period of 5 years after the date of the most recent. A functional variant (equivalent) of mAb7E has essentially the same epitope-binding specificity as mAb7E and exhibits at least 20% (e.g., 30%, 40%, 50%, 60%, 70%, 80%, 90%, or greater) of the activity of neutralizing a signaling pathway mediated by IL-20 as relative to mAb7E. In some embodiments, a functional variant of mAb7E contains the same regions/residues responsible for antigen-binding as mAb7E, such as the same specificity-determining residues in the CDRs or the whole CDRs. The regions/residues that are responsible for antigen-binding can be identified from amino acid sequences of the heavy chain/light chain sequences of mAb7GW or mAb51D (shown above) by methods known in the art. See, e.g., www.bioinf.org.uk/abs; Almagro, J. Mol. Recognit. 17:132-143 (2004); and Chothia et al., J. Mol. Biol. 227: 799-817 (1987).

In one embodiment, the IL-20 cytokines antagonist or/and the IL-20RB receptor antagonist is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library. The random sequence library is obtainable by combinatorial chemical synthesis of DNA. In this library, each member is a linear oligomer, eventually chemically modified, of a unique sequence. Peptide aptamers consists of a conformationally constrained antibody variable region displayed by a platform protein, such as *E. coli* Thioredoxin A that are selected from combinatorial libraries by two hybrid methods.

In some embodiments, the IL-20 cytokines antagonist or/and the IL-20RB receptor antagonist is a polypeptide.

In a particular embodiment the polypeptide is a functional equivalent of IL-20RB receptor. As used herein, a "functional equivalent" of IL-20RB receptor is a compound which is capable of binding to IL-20, thereby preventing its interaction with IL-20RB receptor. The term "functional equivalent" includes fragments, mutants, and muteins of IL-20RB receptor. The term "functionally equivalent" thus includes any equivalent of IL-20RB obtained by altering the amino acid sequence, for example by one or more amino acid deletions, substitutions or additions such that the protein analogue retains the ability to bind to IL-20. Amino acid substitutions may be made, for example, by point mutation of the DNA encoding the amino acid sequence.

In some embodiments, the polypeptide of the present invention is fused to a heterologous polypeptide to form a fusion protein. As used herein, a "fusion protein" comprises all or part (typically biologically active) of a polypeptide of the present invention operably linked to a heterologous polypeptide (i.e., a polypeptide other than the same polypeptide). Within the fusion protein, the term "operably linked" is intended to indicate that the polypeptide of the present invention and the heterologous polypeptide are fused in-frame to each other. The heterologous polypeptide can be fused to the N-terminus or C-terminus of the polypeptide of the present invention. In some embodiment, the heterologous polypeptide is fused to the C-terminal end of the polypeptide of the present invention.

The polypeptides of the invention may be produced by any suitable means, as will be apparent to those of skill in the art. In order to produce sufficient amounts of polypeptides for use in accordance with the present invention, expression may conveniently be achieved by culturing under appropriate conditions recombinant host cells containing the polypeptide of the invention. In particular, the polypeptide is produced by recombinant means, by expression from an encoding nucleic acid molecule. Systems for cloning and expression of a polypeptide in a variety of different host cells are well known. When expressed in recombinant form, the polypeptide is in particular generated by expression from an encoding nucleic acid in a host cell. Any host cell may be used, depending upon the individual requirements of a particular system. Suitable host cells include bacteria mammalian cells, plant cells, yeast and baculovirus systems. Mammalian cell lines available in the art for expression of a heterologous polypeptide include Chinese hamster ovary cells. HeLa cells, baby hamster kidney cells and many others. Bacteria are also preferred hosts for the production of recombinant protein, due to the ease with which bacteria may be manipulated and grown. A common, preferred bacterial host is *E coli*.

The polypeptides of the invention, fragments thereof and fusion proteins (e.g. immunoadhesin) according to the invention can exhibit post-translational modifications, including, but not limited to glycosylations, (e.g., N-linked or O-linked glycosylations), myristylations, palmitylations, acetylations and phosphorylations (e.g., serine/threonine or tyrosine).

In some embodiments, it is contemplated that polypeptides used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. In example adding dipeptides can improve the penetration of a circulating agent in the eye through the blood retinal barrier by using endogenous transporters.

In some embodiment, the IL-20 cytokines antagonist or/and the IL-20RB receptor antagonist is an inhibitor of expression. In particular, the IL-20 cytokines antagonist or/and the IL-20RB receptor antagonist is an inhibitor of IL-20 cytokines gene expression or an inhibitor of IL-20RB receptor gene expression, respectively. In some embodiments, said inhibitor of gene expression is a siRNA, an antisense oligonucleotide or a ribozyme.

Anti-sense oligonucleotides, including anti-sense RNA molecules and anti-sense DNA molecules, would act to directly block the translation of target gene mRNA by binding thereto and thus preventing protein translation or increasing mRNA degradation, thus decreasing the level of an IL-20 cytokine or IL-20 RB receptor subunit thereof, and thus activity, in a cell. For example, antisense oligonucleotides complementary to unique regions of the mRNA transcript sequence encoding IL-20 or IL-20RB can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can function as inhibitors of IL-20RB gene expression or IL-20 cytokines gene expression for use in the present invention. IL-20RB or IL-20 cytokines gene expression can be reduced by contacting a subject or cell with a small double stranded RNA (dsRNA), or a vector or construct causing the production of a small double stranded RNA, such that IL-20RB or IL-20 cytokines gene expression is specifically inhibited (i.e. RNA interference or RNAi). Methods for selecting an appropriate dsRNA or dsRNA-encoding vector are well known in the art for genes whose sequence is known (e.g. see for example Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of IL-20RB gene expression or IL-20 cytokines gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of IL-20RB mRNA sequences or IL-20 cytokines mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of IL-20RB gene expression or IL-20 cytokines gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing IL-20RB or IL-20 cytokines. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art. Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991. Preferred viruses for certain applications are the adeno-viruses and adeno-associated viruses, which are double-stranded DNA viruses. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion. Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, eye, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or ribozyme nucleic acid sequence is under the control of a heterologous regulatory region, e.g., a heterologous promoter.

In some embodiments, the IL-20 cytokines antagonist or/and the IL-20RB receptor antagonist of the invention is administered to the subject with a therapeutically effective amount.

The terms "administer" or "administration" refer to the act of injecting or otherwise physically delivering a substance as it exists outside the body (e.g., the IL-20 cytokines antagonist or/and the IL-20RB receptor antagonist of the present invention) into the subject, such as by mucosal, intradermal, intravenous, subcutaneous, intramuscular delivery and/or any other method of physical delivery described herein or known in the art. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

By a "therapeutically effective amount" is meant a sufficient amount of IL-20 cytokines antagonist or/and IL-20RB receptor antagonist to prevent for use in a method for the treatment of pulmonary bacterial infections at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The compositions according to the invention are formulated for parenteral, transdermal, oral, rectal, intrapulmonary, subcutaneous, sublingual, topical or intranasal administration. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

In a one embodiment, the compositions according to the invention are formulated for intrapulmonary/intranasal administration.

In a preferred embodiment, the compositions according to the invention are formulated for intravenous administration.

In one embodiment, the compositions according to the invention are formulated for parental administration. The pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

Typically the active ingredient of the present invention (i.e. the IL-20 cytokines antagonist or/and the IL-20RB receptor antagonist) is combined with pharmaceutically acceptable excipients, and optionally sustained-release matrices, such as biodegradable polymers, to form pharmaceutical compositions. The term "pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. In the pharmaceutical compositions of the present invention, the active ingredients of the invention can be administered in a unit administration form, as a mixture with conventional pharmaceutical supports.

In some embodiments, the IL-20 cytokines antagonist or/and the IL-20RB receptor antagonist of the present invention is administered to the subject in combination with another active ingredient. In some embodiments, the IL-20 cytokines antagonist or/and the IL-20RB receptor antagonist of the present invention is administered to the subject in combination with a standard treatment. For instance, standard treatment of pulmonary bacterial infections is antibacterial agent, such as antibiotics. Suitable antibiotics that could be coadministered in combination with the IL-20 cytokines antagonist or/and the IL-20RB receptor antagonist include, but are not limited to, at least one antibiotic selected from the group consisting of: ceftriaxone, cefotaxime, vancomycin, meropenem, cefepime, ceftazidime, cefuroxime, nafcillin, oxacillin, ampicillin, ticarcillin, ticarcillin/clavulinic acid (Timentin), ampicillin/sulbactam (Unasyn), azithromycin, trimethoprim-sulfamethoxazole, clindamycin, ciprofloxacin, levofloxacin, synercid, amoxicillin, amoxicillin/clavulinic acid (Augmentin), cefuroxime, trimethoprim/sulfamethoxazole, azithromycin, clindamycin, dicloxacillin, ciprofloxacin, levofloxacin, cefixime, cefpodoxime, loracarbef, cefadroxil, cefabutin, cefdinir, and cephradine. Combination treatment may also include respiratory anti-inflammatory compounds. Examples of corticosteroids that can be used in combination with the IL-20 cytokines antagonist or/and the IL-20RB receptor antagonist are prednisolone, methylprednisolone, dexamethasone, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, deprodone propionate, fluticasone propionate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate and hydrocortisone probutate. Particularly preferred corticosteroids under the present invention are: dexamethasone, budesonide, beclomethasone, triamcinolone, mometasone, ciclesonide, fluticasone, flunisolide, dexamethasone sodium phosphate and esters thereof as well as 6α,9α-difluoro-17α-[(2-furanylcarbonyl)oxy]-11β-hydroxy-16α-methyl-3-oxoandrosta-1,4-diene-17β-carbothioic acid (S)-fluoromethyl ester. Still more preferred corticosteroids under the present invention are: budesonide, beclomethasone dipropionate, mometasone furoate, ciclesonide, triamcinolone, triamcinolone acetonide, triamcinolone hexaacetonide and fluticasone propionate optionally in the form of their racemates, their enantiomers, their diastereomers and mixtures thereof, and optionally their pharmacologically-compatible acid addition salts. Even more preferred are budesonide, beclomethasone dipropionate, mometasone furoate, ciclesonide and fluticasone propionate. Combination treatment may also include bronchodilator. Examples of bronchodilators that can be used in combination with the IL-20 cytokines antagonist or/and the IL-20RB receptor antagonist include but are not limited to β2-agonists (e.g. salbutamol, bitolterol mesylate, formoterol, isoproterenol, levalbuterol, metaproterenol, salmeterol, terbutaline, and fenoterol), anticholinergic (e.g. tiotropium or ipratropium), methylxanthined, and phosphodiesterase inhibitors. In some embodiments, the antagonist of the invention is administered to the subject in combination with a vaccine which contains an antigen or antigenic composition capable of eliciting an immune response against a bacterium. For instance, the vaccine composition is directed against Streptococcus pneumonia. Typically, vaccine composition typically contains whole killed or inactivated (eg., attenuated) bacteria isolate(s). However, soluble or particulate antigen comprising or consisting of outer cell membrane and/or surface antigens can be suitable as well, or instead of, whole killed organisms. In one or more embodiments, the outer cellular membrane fraction or membrane protein(s) of the selected isolate(s) is used. For instance, NTHi OMP P6 is a highly conserved 16-kDa lipoprotein (Nelson, 1988) which is a target of human bactericidal antibody and induces protection both in humans and in animal models. Accordingly, OMP P6 or any other suitable outer membrane NTHi proteins, polypeptides (eg., P2, P4 and P26) or antigenic fragments of such proteins or polypeptides can find application for a NTHi vaccine. Soluble and/or particulate antigen can be prepared by disrupting killed or viable selected isolate(s). A fraction for use in the vaccine can then be prepared by centrifugation, filtration and/or other appropriate techniques known in the art. Any method which achieves the required level of cellular disruption can be employed including sonication or dissolution utilizing appropriate surfactants and agitation, and combination of such techniques. When sonication is employed, the isolate can be subjected to a number of sonication steps in order to obtain the required degree of cellular disruption or generation of soluble and/or particulate matter of a specific size or size range. In some embodiments, the vaccine composition comprises an adjuvant, in a particular TLR agonist. In one embodiment, the TLR agonist is selected from the group consisting of TLR1, TLR2, TLR3, TLR4, TLR5, TLR6, TLR7, TLR8, TLR9, TLR10, TLR11, TLR12, or TLR13 agonists. In certain embodiments, oxygen requirements may increase and supplemental oxygen may be provided.

The invention will be further illustrated by the following figures and examples. However, these examples and figures should not be interpreted in any way as limiting the scope of the present invention.

FIGURES

FIG. 1: Induction of the expression of IL-19, IL-20 and IL-24 as well as IL-22 and their receptors (IL-20RA and IL-20Rb) by infection with *Streptococcus pneumoniae* (SP) in the lung of wild type mice, 24 h after infection. The expression of the mRNA encoding for these cytokines and receptors was measured by qRT-PCR and expressed as the relative expression compared with control mice (receiving PBS) calculated by the 2-ΔΔCt method (mean±SEM).

FIG. 2: Preventive treatment with blocking anti-IL-20Rb antibody decreased the bacterial load in the bronchoalveolar lavage (BAL), the lung tissue and the blood at both 24 and 48h in mice infected with *Streptococcus pneumoniae* (SP). The results are expressed as the number of colony forming unit (cfu)/ml for each compartment (mean±SEM).

FIG. 3: Preventive treatment with blocking anti-IL-20Rb antibody reduced the total number of cells in the broncho-alveolar lavage (BAL) and the lung tissue from mice infected with *Streptococcus pneumoniae* (SP). The number of cells was reported in both compartments at 24 and 48 h after infection with SP (mean±SEM).

FIG. 4: Preventive treatment with blocking anti-IL-20Rb antibody decreased the number of inflammatory cells in the lung tissue of mice infected with *Streptococcus pneumoniae* (SP). The number of cells was reported at 24 and 48 h after infection with SP and expressed as mean±SEM.

FIG. 5: Preventive treatment with blocking anti-IL-20Rb antibody inhibited the production of the cytokines IL-6, IFN-γ and IL-17 in mice infected by *Streptococcus pneumoniae* (SP), in the bronchoalveolar lavage (BAL) and the lung lysates. The levels of cytokines were measured by ELISA at both 24 and 48h after infection with SP. The results were expressed as the mean±SEM of the levels expressed in pg/ml.

EXAMPLE

Material & Methods

Six- to eight-week-old male wild-type (WT) C57BL/6 (H-2D$^b$) mice were purchased from Janvier (Le Genest-St-Isle, France). All animal work conformed to the guidelines of Animal Care and Use Committee from Nord Pas-de-Calais (agreement no. AF 16/20090). Mice were inoculated by the intranasal route with a clinical isolate of *Streptococcus pneumoniae* (Sp) serotype 1 described elsewhere (Marques, J. M. et al 2012. *Immunobiology* 217:420-429). Mice were anesthetized and administered intranasally with 10$^6$ Colony-forming units (CFU) of *Streptococcus pneumoniae* in 50 µl. When indicated mice were treated 24 h before and 24 h after the infection with 50 µg/mice of a blocking rat monoclonal anti-IL-20RB antibody (Clone 20RNTC, Affymetrix) by the intra-peritoneal route.

Mice were daily monitored for illness and mortality. Bacterial burden in the broncho-alveolar lavages (BAL), lungs and blood was measured by plating samples onto chocolate plates collected after 24 and 48 hours. CFU were enumerated 24 hours later. Lung inflammation was analyzed in the BAL and lungs. Total cell numbers per BAL was determined. Pulmonary cells were prepared by enzymatic digestion and were analyzed by flow cytometry. The expression of IL-20 cytokines (IL-19, IL-20, IL-24), of IL-22 and their receptors (IL-20RA and IL-20RB) was analyzed by quantitative RT-PCR in the lung tissues. The results were expressed as a relative expression (calculated by the $2^{-\Delta\Delta Ct}$ method) in comparison with the level obtained in mice exposed to PBS alone. Cytokine secretion was also analyzed in the BAL and the lung lysates. Cytokine concentrations were analyzed for IL-6, IFN-γ and IL-17 by ELISA (Affymetrix).

Results

Figure 1:
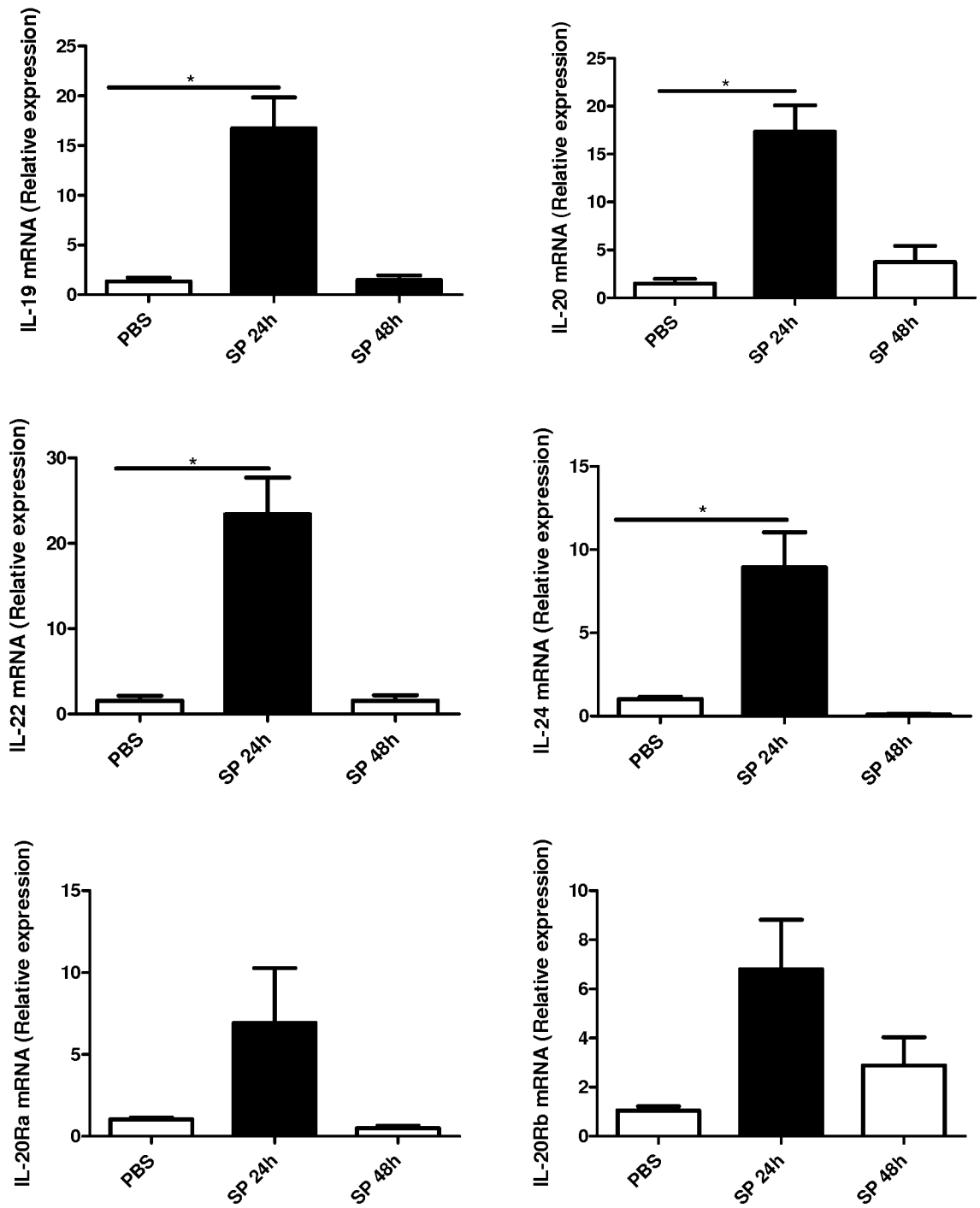
FIG. 1 shows that the expression of IL-19, IL-20 and IL-24 as well as IL-22 and their receptors (IL-20RA and IL-20RB) was induced by infection with *S. pneumoniae* in the lung of wild type mice, 24 h after infection. These levels returned to baseline at 48 h after infection.
Figure 2:
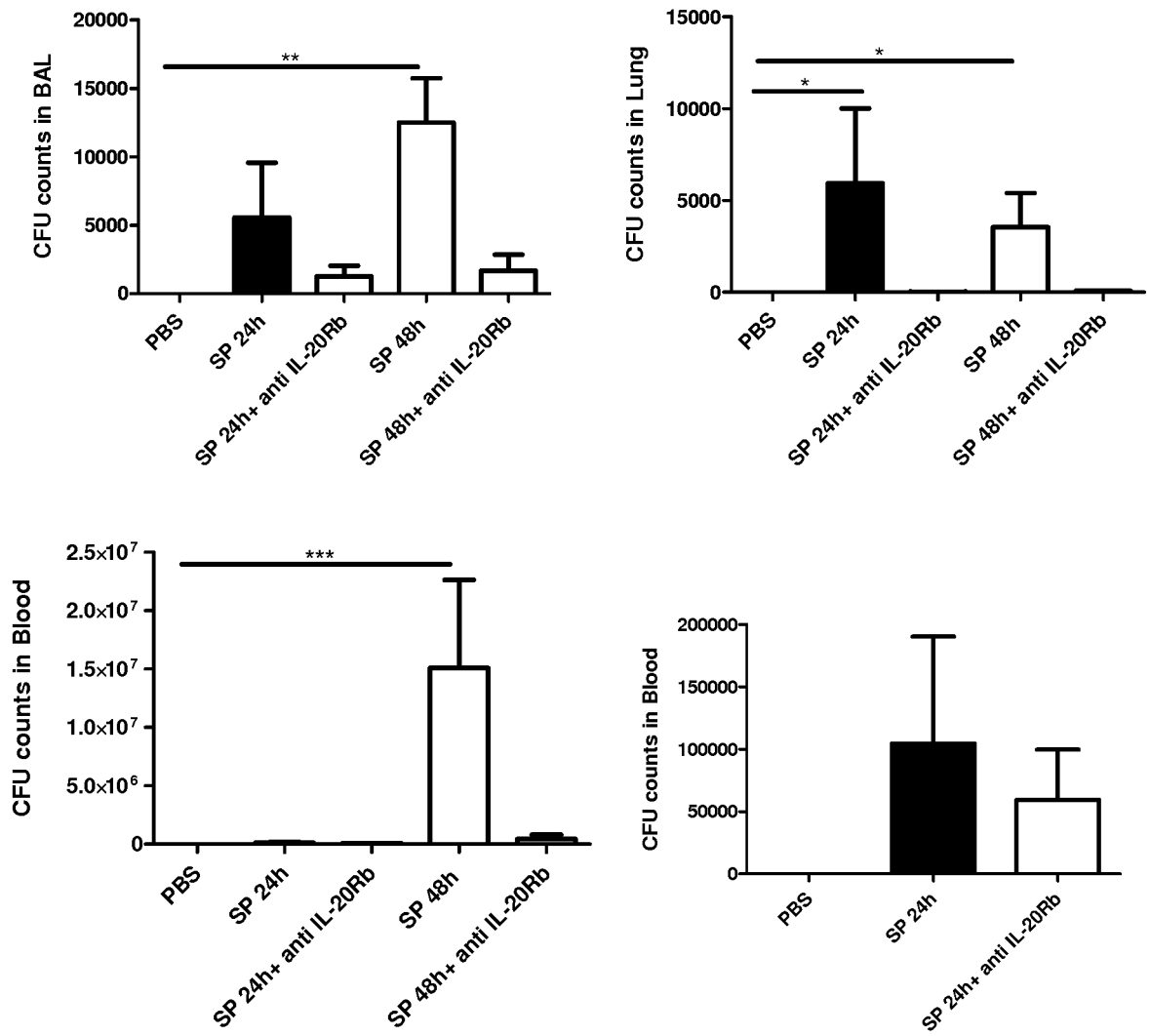
FIG. 2 shows that preventive treatment with blocking anti-IL-20Rb antibody decreased the bacterial load in the bronchoalveolar lavage (BAL), the lung tissue and the blood at both 24 and 48 h in mice infected with *Streptococcus pneumoniae*.
Figure 3:
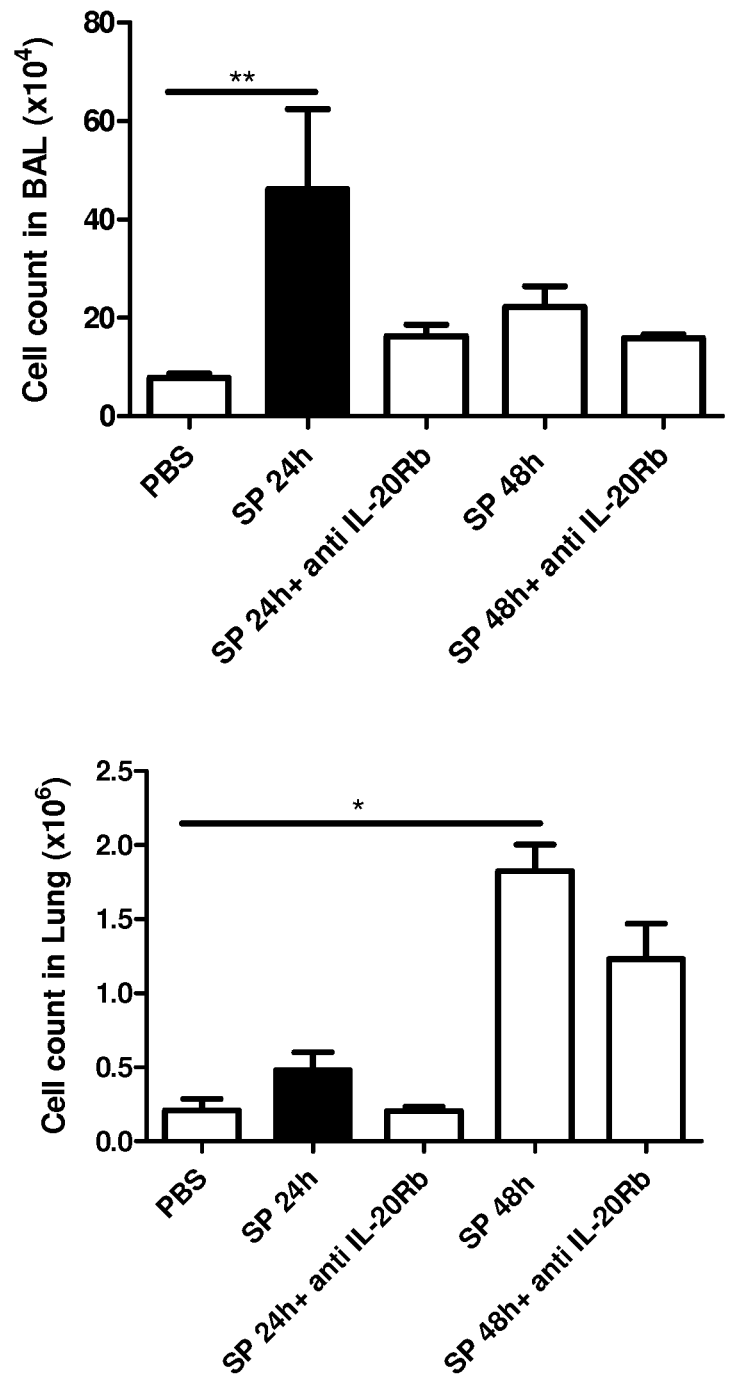

Preventive treatment with blocking anti-IL-20Rb antibody reduced the total number of cells in the bronchoalveolar lavage (BAL) and the lung tissue from mice infected with *S. pneumoniae* (FIG. 3).

Figure 4:
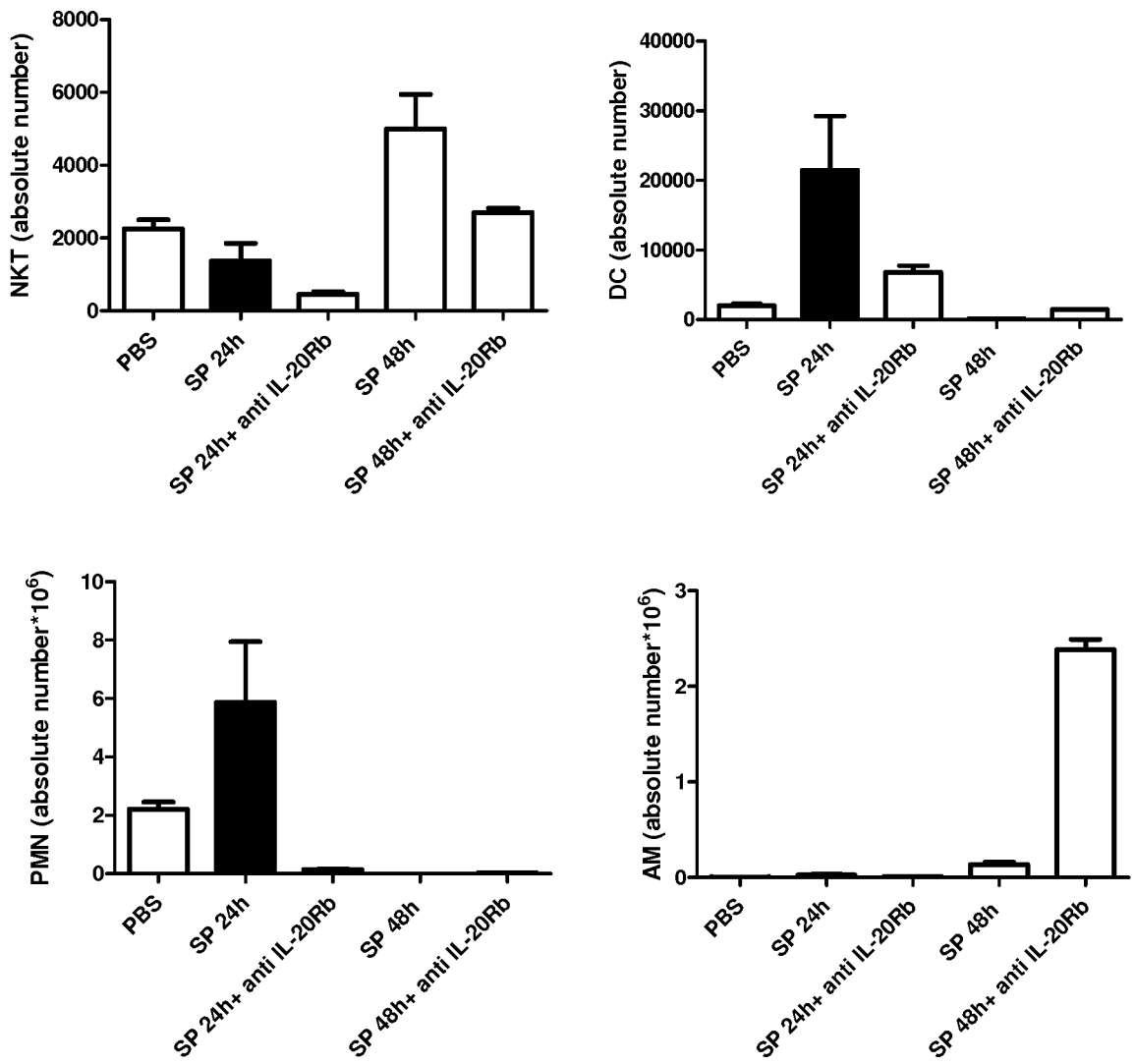

FIG. 4 shows that preventive treatment with blocking anti-IL-20Rb antibody decreased the number of inflammatory cells in the lung tissue of mice infected with *S. pneumoniae*. The number of natural killer T cells (NKT), dendritic cells (DC), polymorphonuclear neutrophils (PMN) determined by flow cytometry were decreased by this treatment whereas those of alveolar macrophages (AM) were increased.

Figure 5:
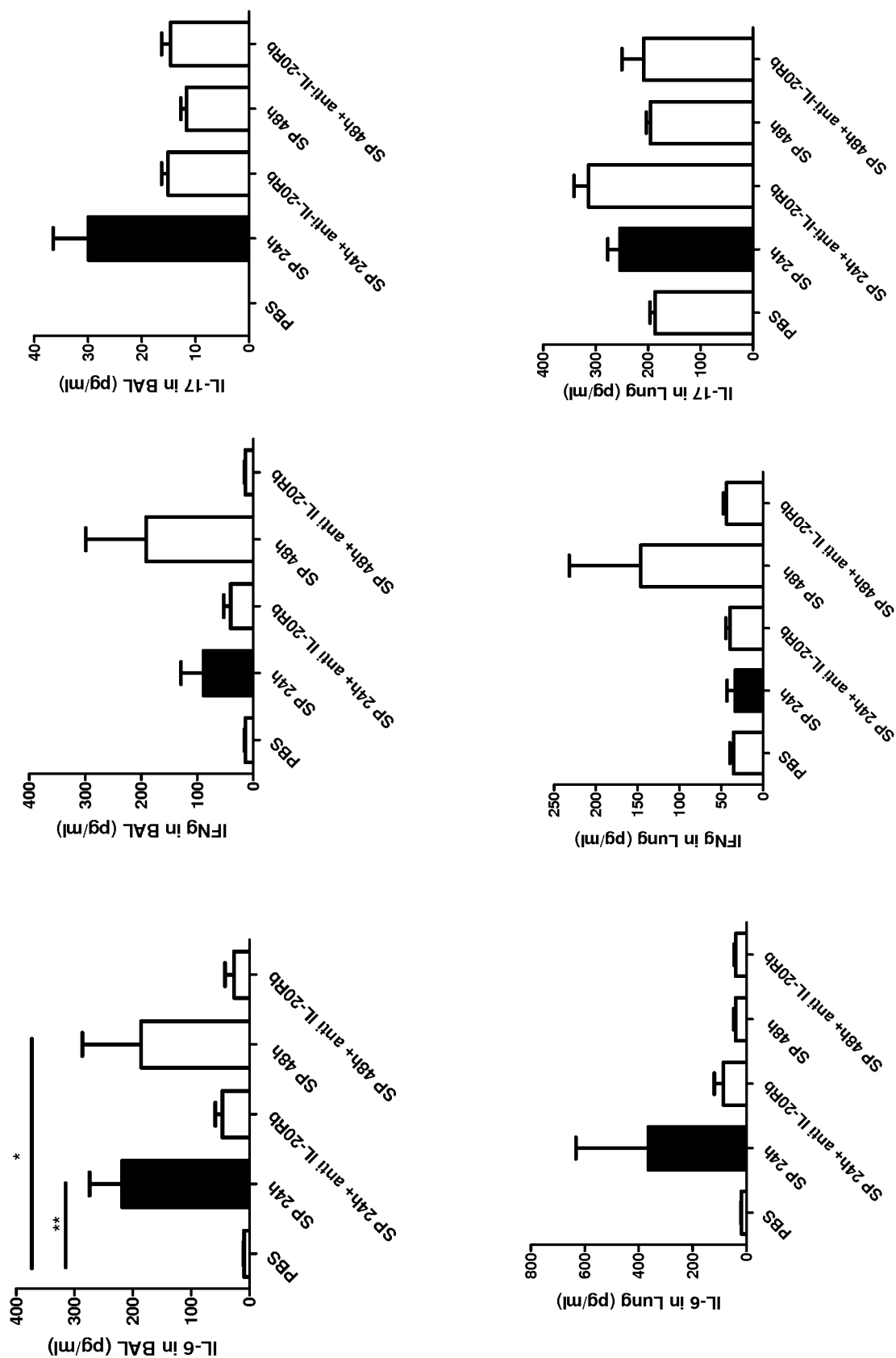

Preventive treatment with blocking anti-IL-20Rb antibody inhibited the production of the cytokines IL-6, IFN-γ and IL-17 in mice infected by *S. pneumoniae*, in the bronchoalveolar lavage (BAL) and the lung lysates (FIG. 5).

Altogether, these data showed that infection with SP increased the expression of IL-20 cytokines and their receptors at 24 h post-infection. Moreover, preventive treatment with anti-IL-20RB antibody markedly inhibit the bacterial burden in the lung and the blood as well as the lung inflammatory reaction.

References:

Throughout this application, various references describe the state of the art to which this invention pertains. The disclosures of these references are hereby incorporated by reference into the present disclosure.

The invention claimed is:

1. A method of decreasing a bacterial load from a pulmonary bacterial infection in a subject in need thereof comprising administering to the subject an antagonist of IL-20 cytokines or/and an antagonist of IL-20RB receptor in an amount sufficient to decrease the bacterial load.

2. The method of claim 1 wherein the IL-20 cytokines antagonist or/and the IL-20RB receptor antagonist is an antibody.

3. The method according to claim 1, wherein the IL-20 cytokines antagonist or/and the IL-20RB receptor antagonist is administered to the subject in combination with antibiotics.

4. The method according to claim 1, wherein the IL-20 cytokines antagonist or/and the IL-20RB receptor antagonist is administered to the subject in combination with corticosteroids.

5. The method according to claim 1, wherein the IL-20 cytokines antagonist or/and the IL-20RB receptor antagonist is administered to the subject in combination with a bronchodilator.

6. The method according claim 1, wherein the IL-20 cytokines antagonist or/and the IL-20RB receptor antagonist is administered to the subject in combination with a vaccine.

7. The method according to claim 1, wherein the pulmonary infection is caused by a bacteria selected from the group consisting of the *Aquaspirillum* family, *Azospirillum* family, *Azotobacteraceae* family, *Bacteroidaceae* family, *Bartonella* species, *Bdellovibrio* family, *Campylobacter* species, *Chlamydia* species, *Clostridium*, *Enterobacteriaceae* family, *Gardinella* family, *Haemophilus influenzae*, *Halobacteriaceae* family, *Helicobacter* family, *Legionallaceae* family, *Listeria* species, *Methylococcaceae* family, mycobacteria, *Neisseriaceae* family, *Oceanospirillum* family, *Pasteurellaceae* family, *Pneumococcus* species, *Pseudomonas* species, *Rhizobiaceae* family, *Spirillum* Family, *Spirosomaceae* family, *Staphylococcus, Streptococcus, Vampirovibr Helicobacter* Family, and *Vampirovibrio* family.

8. The method of claim 2 wherein the antibody is a chimeric antibody, a humanized antibody or full human monoclonal antibody.

\* \* \* \* \*

SEQUENCE LISTING

<160> NUMBER OF SEQ ID NOS: 11

<210> SEQ ID NO 1
<211> LENGTH: 311
<212> TYPE: PRT
<213> ORGANISM: Homo sapiens

<400> SEQUENCE: 1

Met Gln Thr Phe Thr Met Val Leu Glu Glu Ile Trp Thr Ser Leu Phe
1               5                   10                  15

Met Trp Phe Phe Tyr Ala Leu Ile Pro Cys Leu Leu Thr Asp Glu Val
            20                  25                  30

Ala Ile Leu Pro Ala Pro Gln Asn Leu Ser Val Leu Ser Thr Asn Met
        35                  40                  45

Lys His Leu Leu Met Trp Ser Pro Val Ile Ala Pro Gly Glu Thr Val
    50                  55                  60

Tyr Tyr Ser Val Glu Tyr Gln Gly Glu Tyr Ser Leu Tyr Thr Ser
65                  70                  75                  80

His Ile Trp Ile Pro Ser Ser Trp Cys Ser Leu Thr Glu Gly Pro Glu
                85                  90                  95

Cys Asp Val Thr Asp Asp Ile Thr Ala Thr Val Pro Tyr Asn Leu Arg
            100                 105                 110

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Arg Pro Gly Met Glu
    130                 135                 140

Ile Thr Lys Asp Gly Phe His Leu Val Ile Glu Leu Glu Asp Leu Gly
145                 150                 155                 160

Pro Gln Phe Glu Phe Leu Val Ala Tyr Trp Arg Arg Glu Pro Gly Ala
                165                 170                 175

Glu Glu His Val Lys Met Val Arg Ser Gly Gly Ile Pro Val His Leu
            180                 185                 190

Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
    210                 215                 220

Glu Val Gln Gly Glu Ala Ile Pro Leu Val Leu Ala Leu Phe Ala Phe
225                 230                 235                 240

Val Gly Phe Met Leu Ile Leu Val Val Pro Leu Phe Val Trp Lys
                245                 250                 255

Met Gly Arg Leu Leu Gln Tyr Ser Cys Cys Pro Val Val Val Leu Pro
            260                 265                 270

Asp Thr Leu Lys Ile Thr Asn Ser Pro Gln Lys Leu Ile Ser Cys Arg
        275                 280                 285

Arg Glu Glu Val Asp Ala Cys Ala Thr Ala Val Met Ser Pro Glu Glu
    290                 295                 300

Leu Leu Arg Ala Trp Ile Ser
305                 310

<210> SEQ ID NO 2
<211> LENGTH: 147
<212> TYPE: PRT
<213> ORGANISM: Homo sapiens

<400> SEQUENCE: 2

Met Lys His Leu Leu Met Trp Ser Pro Val Ile Ala Pro Gly Glu Thr
1               5                   10                  15

Val Tyr Tyr Ser Val Glu Tyr Gln Gly Glu Tyr Glu Ser Leu Tyr Thr
            20                  25                  30

Ser His Ile Trp Ile Pro Ser Ser Trp Cys Ser Leu Thr Glu Gly Pro
        35                  40                  45

Glu Cys Asp Val Thr Asp Asp Ile Thr Ala Thr Val Pro Tyr Asn Leu
    50                  55                  60

Arg Val Arg Ala Thr Leu Gly Ser Gln Thr Ser Ala Trp Ser Ile Leu
65                  70                  75                  80

Lys His Pro Phe Asn Arg Asn Ser Thr Ile Leu Thr Arg Pro Gly Met
                85                  90                  95

Glu Ile Thr Lys Asp Gly Phe His Leu Val Ile Glu Leu Glu Asp Leu
            100                 105                 110

Gly Pro Gln Phe Glu Phe Leu Val Ala Tyr Trp Arg Arg Glu Pro Gly
        115                 120                 125

Ala Glu Glu Arg Pro Phe Pro Trp Tyr Trp Pro Cys Leu Pro Leu Leu
    130                 135                 140

Ala Ser Cys
145

<210> SEQ ID NO 3
<211> LENGTH: 176
<212> TYPE: PRT
<213> ORGANISM: Homo sapiens

<400> SEQUENCE: 3

Met Lys Ala Ser Ser Leu Ala Phe Ser Leu Leu Ser Ala Ala Phe Tyr
1               5                   10                  15

Leu Leu Trp Thr Pro Ser Thr Gly Leu Lys Thr Leu Asn Leu Gly Ser
            20                  25                  30

Cys Val Ile Ala Thr Asn Leu Gln Glu Ile Arg Asn Gly Phe Ser Glu
        35                  40                  45

Ile Arg Gly Ser Val Gln Ala Lys Asp Gly Asn Ile Asp Ile Arg Ile
    50                  55                  60

Leu Arg Arg Thr Glu Ser Leu Gln Asp Thr Lys Pro Ala Asn Arg Cys
65                  70                  75                  80

Cys Leu Leu Arg His Leu Leu Arg Leu Tyr Leu Asp Arg Val Phe Lys
                85                  90                  95

Asn Tyr Gln Thr Pro Asp His Tyr Thr Leu Arg Lys Ile Ser Ser Leu
            100                 105                 110

Ala Asn Ser Phe Leu Thr Ile Lys Lys Asp Leu Arg Leu Cys His Ala
        115                 120                 125

His Met Thr Cys His Cys Gly Glu Glu Ala Met Lys Lys Tyr Ser Gln
    130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Glu Thr Glu
                165                 170                 175

<210> SEQ ID NO 4
<211> LENGTH: 151
<212> TYPE: PRT
<213> ORGANISM: Homo sapiens

<400> SEQUENCE: 4

Met Lys Ala Ser Ser Leu Ala Phe Ser Leu Leu Ser Ala Ala Phe Tyr
1               5                   10                  15

Leu Leu Trp Thr Pro Ser Thr Gly Leu Lys Thr Leu Asn Leu Gly Ser
            20                  25                  30

Cys Val Ile Ala Thr Asn Leu Gln Glu Ile Arg Asn Gly Phe Ser Glu
        35                  40                  45

Ile Arg Gly Ser Val Gln Ala Lys Asp Gly Asn Ile Asp Ile Arg Ile
    50                  55                  60

Leu Arg Arg Thr Glu Ser Leu Gln Asp Thr Lys Pro Ala Asn Arg Cys
65                  70                  75                  80

Cys Leu Leu Arg His Leu Leu Arg Leu Tyr Leu Asp Arg Val Phe Lys
                85                  90                  95

Asn Tyr Gln Thr Pro Asp His Tyr Thr Leu Arg Lys Ile Ser Ser Leu
            100                 105                 110

Ala Asn Ser Phe Leu Thr Ile Lys Lys Asp Leu Arg Leu Cys Leu Glu
        115                 120                 125

Pro Gln Ala Ala Val Val Lys Ala Leu Gly Glu Leu Asp Ile Leu Leu
    130                 135                 140

Gln Trp Met Glu Glu Thr Glu
145                 150

<210> SEQ ID NO 5
<211> LENGTH: 177
<212> TYPE: PRT
<213> ORGANISM: Homo sapiens

<400> SEQUENCE: 5

Met Lys Leu Gln Cys Val Ser Leu Trp Leu Leu Gly Thr Ile Leu Ile
1               5                   10                  15

Leu Cys Ser Val Asp Asn His Gly Leu Arg Arg Cys Leu Ile Ser Thr
            20                  25                  30

Asp Met His His Ile Glu Glu Ser Phe Gln Glu Ile Lys Arg Ala Ile
        35                  40                  45

Gln Ala Lys Asp Thr Phe Pro Asn Val Thr Ile Leu Ser Thr Leu Glu
    50                  55                  60

Thr Leu Gln Ile Ile Lys Pro Leu Asp Val Cys Cys Val Thr Lys Asn
65                  70                  75                  80

Leu Leu Ala Phe Tyr Val Asp Arg Val Phe Lys Asp His Gln Glu Pro
                85                  90                  95

Asn Pro Lys Ile Leu Arg Lys Ile Ser Ser Ile Ala Asn Ser Phe Leu
            100                 105                 110

Tyr Met Gln Lys Thr Leu Arg Gln Cys Gln Glu Gln Arg Gln Cys His
        115                 120                 125

Cys Arg Gln Glu Ala Thr Asn Ala Thr Arg Val Ile His Asp Asn Tyr
    130                 135                 140

Asp Gln Leu Glu Val His Ala Ala Ala Ile Lys Ser Leu Gly Glu Leu
145                 150                 155                 160

Asp Val Phe Leu Ala Trp Ile Asn Lys Asn His Glu Val Met Phe Ser
                165                 170                 175

Ala

<210> SEQ ID NO 6
<211> LENGTH: 215
<212> TYPE: PRT

<213> ORGANISM: Homo sapiens

<400> SEQUENCE: 6

Met Cys Thr Glu Gly Ala Phe Pro His Arg Ser Ala Cys Ser Leu Pro
1               5                   10                  15

Leu Thr His Val His Thr His Ile His Val Cys Val Pro Val Leu Trp
            20                  25                  30

Gly Ser Val Pro Arg Gly Met Lys Leu Gln Cys Val Ser Leu Trp Leu
        35                  40                  45

Leu Gly Thr Ile Leu Ile Leu Cys Ser Val Asp Asn His Gly Leu Arg
    50                  55                  60

Arg Cys Leu Ile Ser Thr Asp Met His His Ile Glu Glu Ser Phe Gln
65                  70                  75                  80

Glu Ile Lys Arg Ala Ile Gln Ala Lys Asp Thr Phe Pro Asn Val Thr
                85                  90                  95

Ile Leu Ser Thr Leu Glu Thr Leu Gln Ile Ile Lys Pro Leu Asp Val
            100                 105                 110

Cys Cys Val Thr Lys Asn Leu Leu Ala Phe Tyr Val Asp Arg Val Phe
        115                 120                 125

Lys Asp His Gln Glu Pro Asn Pro Lys Ile Leu Arg Lys Ile Ser Ser
130                 135                 140

Ile Ala Asn Ser Phe Leu Tyr Met Gln Lys Thr Leu Arg Gln Cys Gln
145                 150                 155                 160

Glu Gln Arg Gln Cys His Cys Arg Gln Glu Ala Thr Asn Ala Thr Arg
                165                 170                 175

Val Ile His Asp Asn Tyr Asp Gln Leu Glu Val His Ala Ala Ala Ile
            180                 185                 190

Lys Ser Leu Gly Glu Leu Asp Val Phe Leu Ala Trp Ile Asn Lys Asn
        195                 200                 205

His Glu Val Met Phe Ser Ala
    210                 215

<210> SEQ ID NO 7
<211> LENGTH: 207
<212> TYPE: PRT
<213> ORGANISM: Homo sapiens

<400> SEQUENCE: 7

Met Lys Leu Gln Cys Val Ser Leu Trp Leu Leu Gly Thr Ile Leu Ile
1               5                   10                  15

Leu Cys Ser Val Asp Asn His Gly Leu Arg Arg Cys Leu Ile Ser Thr
            20                  25                  30

Asp Met His His Ile Glu Glu Ser Phe Gln Glu Ile Lys Arg Ala Ile
        35                  40                  45

Gln Ala Lys Asp Thr Phe Pro Asn Val Thr Ile Leu Ser Thr Leu Glu
    50                  55                  60

Thr Leu Gln Ile Ile Lys Pro Leu Asp Val Cys Cys Val Thr Lys Asn
65                  70                  75                  80

Leu Leu Ala Phe Tyr Val Asp Arg Val Phe Lys Asp His Gln Glu Pro
                85                  90                  95

Asn Pro Lys Ile Leu Arg Lys Ile Ser Ser Ile Ala Asn Ser Phe Leu
            100                 105                 110

Tyr Met Gln Lys Thr Leu Arg Gln Cys Val Ser His Trp Val Arg Ile
        115                 120                 125

Pro Ala Ser Ala Pro Cys Leu Pro Lys Glu Arg Pro Gly Ser Ala Gly

```
                130                 135                 140
Pro His Arg Pro Pro Asp Met Val Leu Gly Val Lys Gly Asn Ser Leu
145                 150                 155                 160

Arg Thr Ser Thr Gly Arg Thr Val Glu Asn Leu Ser Gln Trp Pro Leu
                165                 170                 175

Leu Pro Gln Gly Ser Leu Pro Ala Asp Asn Ser Ser Asp Gly Leu Leu
                180                 185                 190

Leu Asp Asn Pro Pro Gly Val Thr Asn Leu Cys Gln His Ile Pro
                195                 200                 205
```

<210> SEQ ID NO 8
<211> LENGTH: 206
<212> TYPE: PRT
<213> ORGANISM: Homo sapiens

<400> SEQUENCE: 8

```
Met Asn Phe Gln Gln Arg Leu Gln Ser Leu Trp Thr Leu Ala Arg Pro
1               5                   10                  15

Phe Cys Pro Pro Leu Leu Ala Thr Ala Ser Gln Met Gln Met Val Val
                20                  25                  30

Leu Pro Cys Leu Gly Phe Thr Leu Leu Trp Ser Gln Val Ser Gly
                35                  40                  45

Ala Gln Gly Gln Glu Phe His Phe Gly Pro Cys Gln Val Lys Gly Val
50                  55                  60

Val Pro Gln Lys Leu Trp Glu Ala Phe Trp Ala Val Lys Asp Thr Met
65                  70                  75                  80

Gln Ala Gln Asp Asn Ile Thr Ser Ala Arg Leu Leu Gln Glu Val
                85                  90                  95

Leu Gln Asn Val Ser Asp Ala Glu Ser Cys Tyr Leu Val His Thr Leu
                100                 105                 110

Leu Glu Phe Tyr Leu Lys Thr Val Phe Lys Asn Tyr His Asn Arg Thr
                115                 120                 125

Val Glu Val Arg Thr Leu Lys Ser Phe Ser Thr Leu Ala Asn Asn Phe
130                 135                 140

Val Leu Ile Val Ser Gln Leu Gln Pro Ser Gln Glu Asn Glu Met Phe
145                 150                 155                 160

Ser Ile Arg Asp Ser Ala His Arg Arg Phe Leu Leu Phe Arg Arg Ala
                165                 170                 175

Phe Lys Gln Leu Asp Val Glu Ala Ala Leu Thr Lys Ala Leu Gly Glu
                180                 185                 190

Val Asp Ile Leu Leu Thr Trp Met Gln Lys Phe Tyr Lys Leu
                195                 200                 205
```

<210> SEQ ID NO 9
<211> LENGTH: 207
<212> TYPE: PRT
<213> ORGANISM: Homo sapiens

<400> SEQUENCE: 9

```
Met Asn Phe Gln Gln Arg Leu Gln Ser Leu Trp Thr Leu Ala Ser Arg
1               5                   10                  15

Pro Phe Cys Pro Pro Leu Leu Ala Thr Ala Ser Gln Met Gln Met Val
                20                  25                  30

Val Leu Pro Cys Leu Gly Phe Thr Leu Leu Trp Ser Gln Val Ser
                35                  40                  45

Gly Ala Gln Gly Gln Glu Phe His Phe Gly Pro Cys Gln Val Lys Gly
```

```
                50                  55                  60
Val Val Pro Gln Lys Leu Trp Glu Ala Phe Trp Ala Val Lys Asp Thr
 65                  70                  75                  80

Met Gln Ala Gln Asp Asn Ile Thr Ser Ala Arg Leu Leu Gln Gln Glu
                 85                  90                  95

Val Leu Gln Asn Val Ser Asp Ala Glu Ser Cys Tyr Leu Val His Thr
                100                 105                 110

Leu Leu Glu Phe Tyr Leu Lys Thr Val Phe Lys Asn Tyr His Asn Arg
            115                 120                 125

Thr Val Glu Val Arg Thr Leu Lys Ser Phe Ser Thr Leu Ala Asn Asn
        130                 135                 140

Phe Val Leu Ile Val Ser Gln Leu Gln Pro Ser Gln Glu Asn Glu Met
145                 150                 155                 160

Phe Ser Ile Arg Asp Ser Ala His Arg Arg Phe Leu Leu Phe Arg Arg
                165                 170                 175

Ala Phe Lys Gln Leu Asp Val Glu Ala Ala Leu Thr Lys Ala Leu Gly
            180                 185                 190

Glu Val Asp Ile Leu Leu Thr Trp Met Gln Lys Phe Tyr Lys Leu
        195                 200                 205

<210> SEQ ID NO 10
<211> LENGTH: 154
<212> TYPE: PRT
<213> ORGANISM: Homo sapiens

<400> SEQUENCE: 10

Met Asn Phe Gln Gln Arg Leu Gln Ser Leu Trp Thr Leu Ala Ser Arg
 1               5                  10                  15

Pro Phe Cys Pro Pro Leu Leu Ala Thr Ala Ser Gln Met Gln Met Val
                20                  25                  30

Val Leu Pro Cys Leu Gly Phe Thr Leu Leu Leu Trp Ser Gln Val Ser
            35                  40                  45

Gly Ala Gln Gly Gln Glu Phe His Phe Gly Pro Cys Gln Val Lys Gly
        50                  55                  60

Val Val Pro Gln Lys Leu Trp Glu Ala Phe Trp Ala Val Lys Asp Thr
 65                  70                  75                  80

Met Gln Ala Gln Asp Asn Ile Thr Ser Ala Arg Leu Leu Gln Gln Glu
                 85                  90                  95

Val Leu Gln Asn Val Ser Gln Glu Asn Glu Met Phe Ser Ile Arg Asp
                100                 105                 110

Ser Ala His Arg Arg Phe Leu Leu Phe Arg Arg Ala Phe Lys Gln Leu
            115                 120                 125

Asp Val Glu Ala Ala Leu Thr Lys Ala Leu Gly Glu Val Asp Ile Leu
        130                 135                 140

Leu Thr Trp Met Gln Lys Phe Tyr Lys Leu
145                 150

<210> SEQ ID NO 11
<211> LENGTH: 63
<212> TYPE: PRT
<213> ORGANISM: Homo sapiens

<400> SEQUENCE: 11

Met Asn Phe Gln Gln Arg Leu Gln Ser Leu Trp Thr Leu Ala Ser Lys
 1               5                  10                  15

Leu Arg Ile Thr Ser Arg Val Pro Gly Cys Cys Ser Arg Arg Phe Cys
```

-continued

```
            20                  25                  30
Arg Thr Ser Arg Lys Lys Met Arg Cys Phe Pro Ser Glu Thr Val His
            35                  40                  45
Thr Gly Gly Phe Cys Tyr Ser Gly Glu His Ser Asn Ser Trp Thr
            50                  55                  60
```